United States Patent [19]
Palm et al.

[11] Patent Number: 5,564,573
[45] Date of Patent: Oct. 15, 1996

[54] PROCESS AND APPARATUS FOR THE MACHINE SORTING OF SAWN TIMBER ACCORDING TO STRENGTH

[75] Inventors: Klaus Palm, Grünenplan; Detlev Wienckowski, Coppenbrügge; Martin Steinbach, Gronau, all of Germany

[73] Assignee: Fagus-GreCon Greten GmbH & Co. KG, Alfeld, Germany

[21] Appl. No.: 313,030

[22] PCT Filed: Mar. 10, 1993

[86] PCT No.: PCT/EP93/00547

§ 371 Date: Sep. 23, 1994

§ 102(e) Date: Sep. 23, 1994

[87] PCT Pub. No.: WO93/19355

PCT Pub. Date: Sep. 30, 1993

[30] Foreign Application Priority Data

Mar. 23, 1992 [DE] Germany ............. 42 09 314.7

[51] Int. Cl.$^6$ ................. B07C 5/14; G01L 1/04
[52] U.S. Cl. ............. 209/518; 209/588; 209/589; 209/601; 73/862.451
[58] Field of Search ................. 209/517, 518, 209/519, 520, 587, 588, 599, 600, 601, 602, 604, 589; 271/262, 263; 356/381, 382; 250/560; 73/159, 862.451

[56] References Cited

U.S. PATENT DOCUMENTS

| 4,748,331 | 5/1988 | Nagao et al. ............. 250/560 |
| 5,029,469 | 7/1991 | Chase et al. ............. 73/159 |
| 5,141,110 | 8/1992 | Trischan et al. ............. 209/589 X |
| 5,182,722 | 1/1993 | Hain ............. 209/599 X |

FOREIGN PATENT DOCUMENTS

| 3835486 | 4/1990 | Germany ............. 209/599 |
| 1104986 | 3/1968 | United Kingdom . |
| 2105856 | 3/1983 | United Kingdom . |

OTHER PUBLICATIONS

"Zum gegenwärtigen Stand der maschinellen Holzsortierung", 14 Aug. 1987, Holz-Zentralblat, Stuttgart Nr. 97, p. 1360.

"PSD-Elemente erweitern die optische Messtechnik—Neue Möglichkeiten in der Profilund Schwingungsmessung", 1148 Microtecnic (1991) No. 1, Zurich, CH, pp. 10–13.

Primary Examiner—William E. Terrell
Assistant Examiner—Tuan Nguyen
Attorney, Agent, or Firm—Synnestvedt & Lechner

[57] ABSTRACT

The timber (2) passes in a direction of movement (3) between successive clamping roller pairs (27, 26), between which a test roller (48) imposes a flexible bending $f_D$ on the timber (2). The imposed flexible bending $f_D$ is maintained at least approximately constant by controlling a setting drive (70) by means of a computer (83). Any possible natural curvature of the timber (2) is measured by measuring elements (80, 81) and is taken into account. The thickness (d) of the timber is also measured without contact by measuring elements (81, 82). The restoring force is measured by a force measuring device (68) and the position of the test roller (48) transversely to the direction of movement (3) is measured by a distance transducer (77). From this the commuter (83) calculates the local modulus of elasticity in flexure and combines this, for the final evaluation of the timber (2), with information about strength and density of the timber (2) which results from an irradiation of the timber with a fan shaped beam of radiation (75).

31 Claims, 10 Drawing Sheets

PROCESS AND APPARATUS FOR THE MACHINE SORTING OF SAWN TIMBER ACCORDING TO STRENGTH

BACKGROUND

The invention relates to a process and apparatus for machine sorting of sawn timber according to strength.

In one known process of this type (GB 2105856A) the test roller 9 is set by manual operation of a wheel 15 in dependence upon the type of sawn timber L to be sorted, and that operating position is then not changed thereafter. The shaft of the test roller 9 is mounted on a stable arm 13 which itself is pivotally mounted on a shaft 14 of the machine frame 10. The natural curvature of the wood is not measured. Instead, each piece of timber is turned through 180° about its longitudinal axis after the first pass, is transported back to the input of the machine by taking it back through the machine in the opposite direction, and is sent through the machine again in a second pass. This is time-consuming and operationally costly and can lead to an overstressing of the wood if the wood has natural curvature. Also, the rotary drives of the driven clamping rollers 2, 4 must be reversible.

From GB 1104986 is known a process in which only one pair of rotatably drivable rollers 2, 4 is provided, one of which rollers 4 can be transversely biassed 5. A stationary support roller 3 is positioned at the side of the stationary roller 2 and is spaced from it. At the side of the biassable roller 4, between the roller pair 2, 4 and the support roller 3, is a test roller 7 which is arranged to be urged with constant force (page 2, line 115) against the sawn timber by means of a drive 8. The effective bending deflection of the timber resulting from this is detected by a sensing element 9 which is in contact with the opposite side of the timber and is converted into appropriate electrical signals by means of micro switches 11, with these signals being passed to an evaluation circuit. The effective bending deflection can be falsified by a natural curvature of the timber. Consequently, in advance of the roller pair 2, 4 a test arm 15 is arranged which is pivotable about the axis of the stationary roller 2. In advance of the roller 2 is arranged a roller 13, stationary on the test arm 15, at the same spacing from the roller 2 as there is between the rollers 2 and 3. The roller 13 is maintained in permanent contact with the wood by means of a biassed 18 counter-roller 14. At the same geometrical position as the sensing element 9 relative to the rollers 2, 3 is arranged a sensing element held by an arm 16 of the test arm 15 for sensing the natural curvature of the timber relative to the rollers 2, 13. The oscillations of the arm 16 relative to the test arm 15 are converted 19 into electrical signals which correspond to the natural curvature. In the evaluation circuit the computation of the natural curvature is effected by the effective bending deflection of the timber measured by the sensing system 9 to 11. The constant pressure force of the test roller 7 does not take into account any changing modulus of elasticity of the timber.

From the journal "Microtecnic" No. 1, 1991, Zürich, Switzerland, pages 10 to 13, Hofmann "PSD Elements Broaden the Optical Measuring Techniques", various optical distance sensors are known for contactless distant measurement.

From the journal "Holz-Zentralblatt" No. 97, 14th Aug. 1987, Stuttgart, Germany, page 1360, Tebbe "The Current State of Machine Quality Sorting", column 3, lines 31 to 53; FIG. 4, there is known a decisive improvement in the sorting using a combination of sorting parameters. It makes possible the combination of modulus of elasticity and knottiness. The knottiness could be determined for example by an irradiation method (microwaves or X-rays).

SUMMARY OF THE INVENTION

It is an object of the invention to improve the throughput and the quality of the sorting of timber according to strength with only one pass of the timber.

This object is achieved in a process providing for the supporting of the timber with two pairs of clamping rollers. A test roller is pressed into contact with the timber between the clamping rollers to impart a bending deflection to the timber. This pressing of the test roller is continuous during the measuring process and controlled so that the bending deflection to the timber remains constant. The restoring force exerted by the timber on the test roller due to the bending deflection is measured. Also measured is the natural curvature of the timber and the position of the test roller. The measurements are used by a computer to calculate the strength of the timber. The throughput is increased because of the fact that only one pass is necessary for each piece of timber. Because the imposed deflection is maintained at least approximately constant, the stress on the timber is maintained within definable limits. It is particularly advantageous that any natural curvature of the timber be detected and computed and that through the results of the computation appropriate compensatory control of the setting of the test roller transversely to the direction of movement of the timber can be made. The measurement of this position of the test roller supplies the computer with real values of the actual position of the test roller. Where the working point for the setting of the test roller is maintained in the optimum region of the stress/extension curve of the timber, the conclusions drawn from the measurement of the restoring force about the strength of the timber are more reliable.

It is of particular advantage that the leading edge of the timber is not unnecessarily loaded or damaged when entering into a pair of clamping rollers. This is assured by adjusting each clamping roller pair to an initial gap from one another which is minimally equal to the thickness of the timber.

Measurements of the curvature and thickness are preferably carried out without contact and can be performed either continuously or periodically.

Testing for local knottiness and for the local density bring the advantage that in this way the strength can be tested also at the beginning and end of the piece of timber, which parts, in the case of a pure bending process, cannot be tested because of the span between supports which is unavoidable with such a process. The evaluation of the measured strength values at the beginning and end of the piece of timber can be taken into account for all special strength conditions which might be encountered. For example in the case of timber which is provided for finger jointing or gang-nail connections and other structural timber with mechanical connecting elements at its ends, the beginning and end must be free from knots and the gross density midst not be less than a specific value.

Using X-rays for determining knottiness and density provides a particularly safe radiation source, which additionally operates cyclically, in other words can be switched off if manufactured data from an irradiation are not necessary. An X-ray apparatus can be shielded and handled comparatively easily in terms of safety of operation.

By the combination of the characteristic values of the local modulus of elasticity and the local knottiness and/or local gross density the reliability and precision of the classification of the timber according to strength can be considerably increased. This leads to a better utilization of the natural material, namely wood, and can on the other hand lead to a reduction in the timber cross-section for the same strength. No limits are placed on the evaluation of the individual measurement value types within the framework of their computerised compilation in order to establish a sorting class. Thus, for example at the beginning and end regions of the timber, special emphasis can be laid on knots and gross density, while in the other regions of the timber special weight is attributed to the bending strength.

One means for achieving this is where the minimum local strength is determined by computer and compared with sorting classes established by bands of strength values, and thereafter the timber is sorted into relevant sorting classes. This makes possible for the commercial users concerned a reliable choice of timber in the individual sorting classes. In conventional manner a marking of the timber can be used to identify these sorting classes.

An even better output from available timber can be made by identifying appropriate qualitative or sorting classes and their limits for use in cutting up and sorting the timber. Thus, the highest possible proportions of the timber can be classified into the highest possible sorting classes. Here again a marking as to the particular sorting class is preferably carried out in order to facilitate the automated subsequent handling of the timber.

The invention also relates to an apparatus for the machine sorting of sawn timber according to strength. One such apparatus is known from the aforementioned GB 2105856A. This machine has the disadvantages which have already been remarked on in terms of the method.

It is therefore also an object of the present invention to improve this apparatus.

This object is achieved by an apparatus having two pairs of clamping rollers for supporting and advancing the timber. In between the clamping roller pairs is a test roller which is moveable into the timber to impose a continuous and constant bending deflection to the timber. A force measuring device measures the restoring force exerted by the timber due to the deflection. The restoring force measurements are used to determine strength. The device also has means for measuring the natural curvature of the timber and the position of the test roller. A controllable setting drive presses the test roller into the timber. The measurements are useable for determining strength and sorting. Substantially the same advantages result for the apparatus as described above in relation to the process.

Each clamping roller pair can have a first clamping roller rotatably fixed, and a second clamping roller on slide means displaceable transversely to the direction of movement of the timber. Each slide means is displaceable by a controllable clamping drive. Here, the longitudinal axes of the clamping rollers of each pair of clamping rollers are preferably arranged parallel to each other. The mounting of the second clamping roller on a slide carriage or alternatively a trolley ensures a particularly precise transverse movement of the second clamping roller which has low friction. A bellows cylinder which is actuated by compressed air and which can be controlled from the computer can be used for example as the clamping drive. Such bellows cylinders are obtainable for example from the company Robert Bosch GmbH of Stuttgart, Germany.

Each clamping drive can be supported by a holder which is pre-settable in the direction of displacement of the associated slide means in dependence upon the particular timber thickness. This shortens the path to be followed by the clamping drive to a minimum. The presetting of the holder can be effected manually by a spindle drive for example.

A defined initial position for the slide means is created wherein between each slide means and the associated holder there is provided spring means by which the slide means is urged in a direction of opening away from the first clamping roller.

Contactless measurement of the curvature as described herein is free from wear and very precise. As measuring components one can use for example "MQ" laser analogue sensors which are supplied by SDS-RELAIS AG, Fichtenstrasse 3-5, D-82041 Deisenhofen, near Munich.

A thickness measurement of the timber is preferably carried out in advance of the pair of clamping rollers which first come into contact with the timber and preferably is effected with the aforementioned laser sensors.

Using radiation there is the possibility of acquiring measurement data in relation to knots and/or gross density in the assessment of the strength of the timber, in addition to the modulus of elasticity in flexure obtained on the basis of the bending of the timber.

An X-ray apparatus and an associated line of receivers can supply image points over the whole width of the timber which when combined together with the adjacent received images makes it possible to build up a very reliable and complete picture. Thus, the position of flaws such as knots and other gross density variations can be accurately identified, evaluated and rated also in transverse direction of the timber.

Where the test roller is rotatably mounted on a slide carriage which is displaceable transversely to the direction of movement of the timber, and a connecting rod incorporating the force measuring device is coupled to the slide carriage and is displaceable by the setting drive which is fixed in position on the apparatus, the test roller is displaceable in the transverse direction in a way which is particularly precise and low in friction. The determination of the restoring force by the force measuring device is correspondingly reliable. Instead of a slide carriage one can alternatively use a trolley here.

Where the setting drive which is fixed in position on the apparatus is connected by means of a connecting rod to a slide carriage which is displaceable transversely to the direction of movement of the timber, and the two ends of the shaft of the test roller are respectively supported on the slide carriage by respective force measuring elements of the force measuring device, a trouble-free force measurement is still guaranteed even if the resulting force exerted by the wood on the test roller is not exerted at the longitudinal centre of the test roller.

Further features and advantages of the invention will now be described in more detail with reference to a number of embodiments which are given by way of example and which are shown in the drawings.

DESCRIPTION OF PREFERRED EMBODIMENTS

Figure 1:
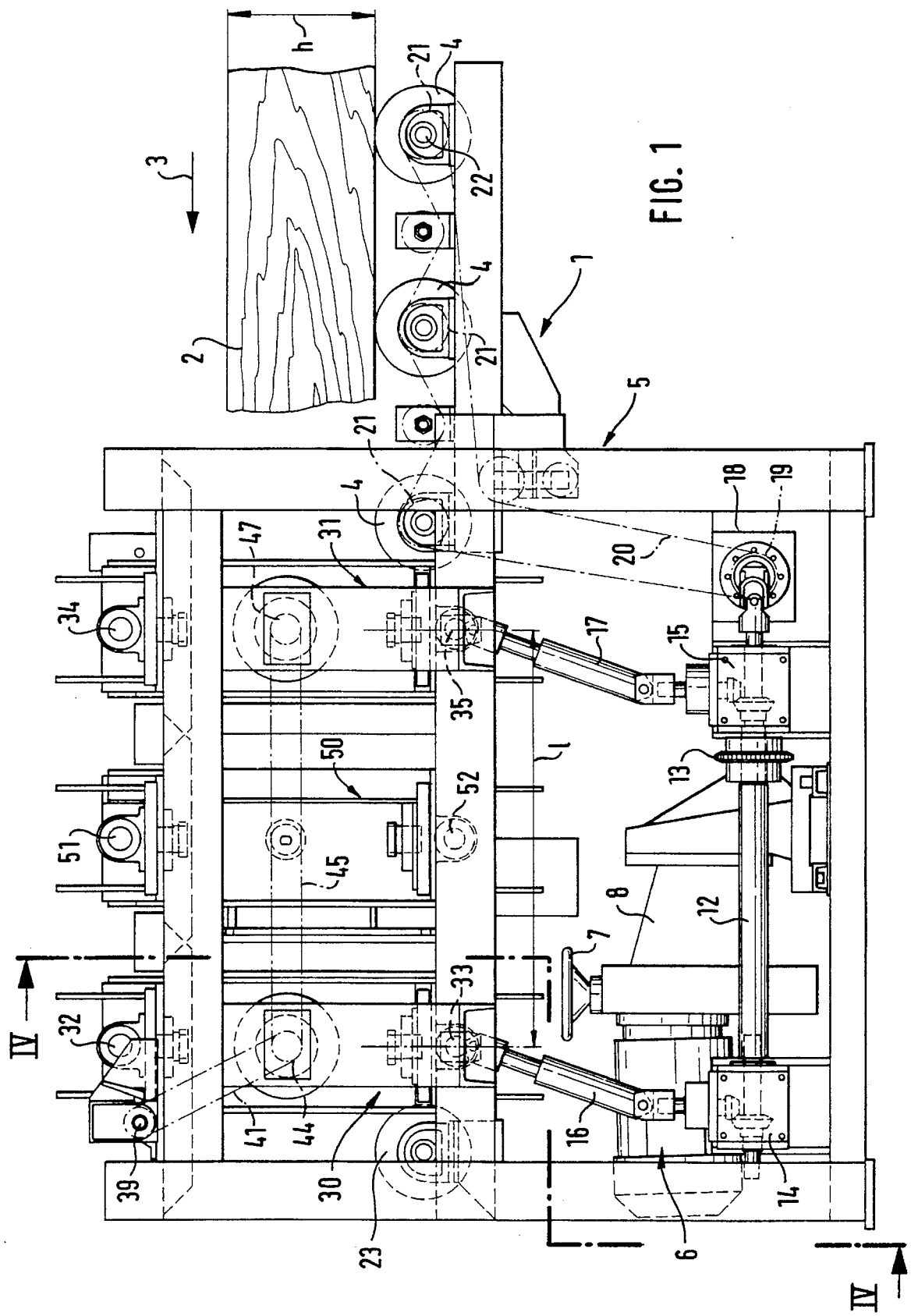
FIG. 1 is a side view of an apparatus for machine sorting of sawn timber according to strength.

FIG. 1 shows an apparatus 1 for the machine sorting of sawn timber 2 according to strength, where the timber enters into the apparatus 1 on edge in a direction of movement 3 on rotationally driven rollers 4.

The apparatus 1 comprises a sturdy frame 5 in which, at the bottom, is mounted a drive unit 6 with a gear unit 8 which is steplessly adjustable by means of a handwheel 7 to vary the drive speed. A take-off shaft 9 (FIG. 3) of the gear unit 8 drives a chain wheel 10 (FIG. 3) which, by means of a chain 11 (FIG. 3), drives a chain wheel 13 which is fixed on a shaft 12. By means of bevel gear units 14 and 15 the shaft 12 drives telescopic universal-joint shafts 16 and 17, and moreover, by means of an angle drive 18, drives a chain wheel 19. By means of a chain 20 the chain wheel 19 drives chain wheels 21 on axles 22 of the rollers 4.

At the output of the apparatus 1 there is located a roller 23 which is not rotationally driven and which is to support the exiting timber 2.

The universal-joint shafts 16, 17 respectively drive a second clamping roller 24 and 25 (FIG. 2) of clamping roller pairs 26 and 27. The clamping roller pairs 26, 27 are arranged spaced from each other in the direction of movement 3 by a distance 1, the so-called support span. Each clamping roller pair 26, 27 also comprises a first clamping roller 28 and 29 respectively (FIG. 2) which is mounted to be rotatable but which is fixed in position on the apparatus.

The longitudinal axes of the clamping rollers 24, 25 and 28, 29 are all arranged to be vertical. The second clamping rollers 24, 25 are rotatably mounted in respective slide carriers 30 and 31. The slide carriers 30, 31 are each displaceable perpendicular to the direction of movement 3 on two horizontal guide rods 32, 33 and 34, 35 respectively which are arranged vertically spaced from one another and which are rigid with the framework. The width h of the timber 2 is indicated in FIG. 1, while the thickness d of the timber can be seen from FIG. 4. In dependence upon the thickness d, the spacing of the clamping rollers 24 and 28 as well as of the clamping rollers 25 and 29 from each other is initially set so that the initial gap 36 (FIG. 3) is somewhat greater than the thickness d of the timber 2. This basic setting is effected synchronously by means of a hand wheel 37 or 38 (FIG. 2), a shaft 39 mounted on the frame 5, a chain wheel 40 (FIG. 2) fixed on the shaft, a chain 41, a chain wheel 43 fixed on a spindle 42 (FIG. 2), an equivalent chain wheel 44 also fixed on the spindle 42, a chain 45 and wheel 44 also fixed on the spindle 42, a chain 45 and another similar chain wheel 47 fixed on a spindle 46. Details of this basic setting will be outlined in connection with FIG. 3.

In the center, between the clamping roller pairs 26, 27 (FIG. 2) is arranged a freely rotatable test roller 48 mounted on a shaft 49 which is parallel to the longitudinal axes of the clamping rollers 24, 25, 28, 29. The test roller 48 is rotatably mounted on a slide carrier 50 which is displaceable on guide rods 51 and 52 perpendicular to the direction of movement 3, with the guide rods being fixed in position on the frame and parallel to the guide rods 32 to 35.

Figure 3:
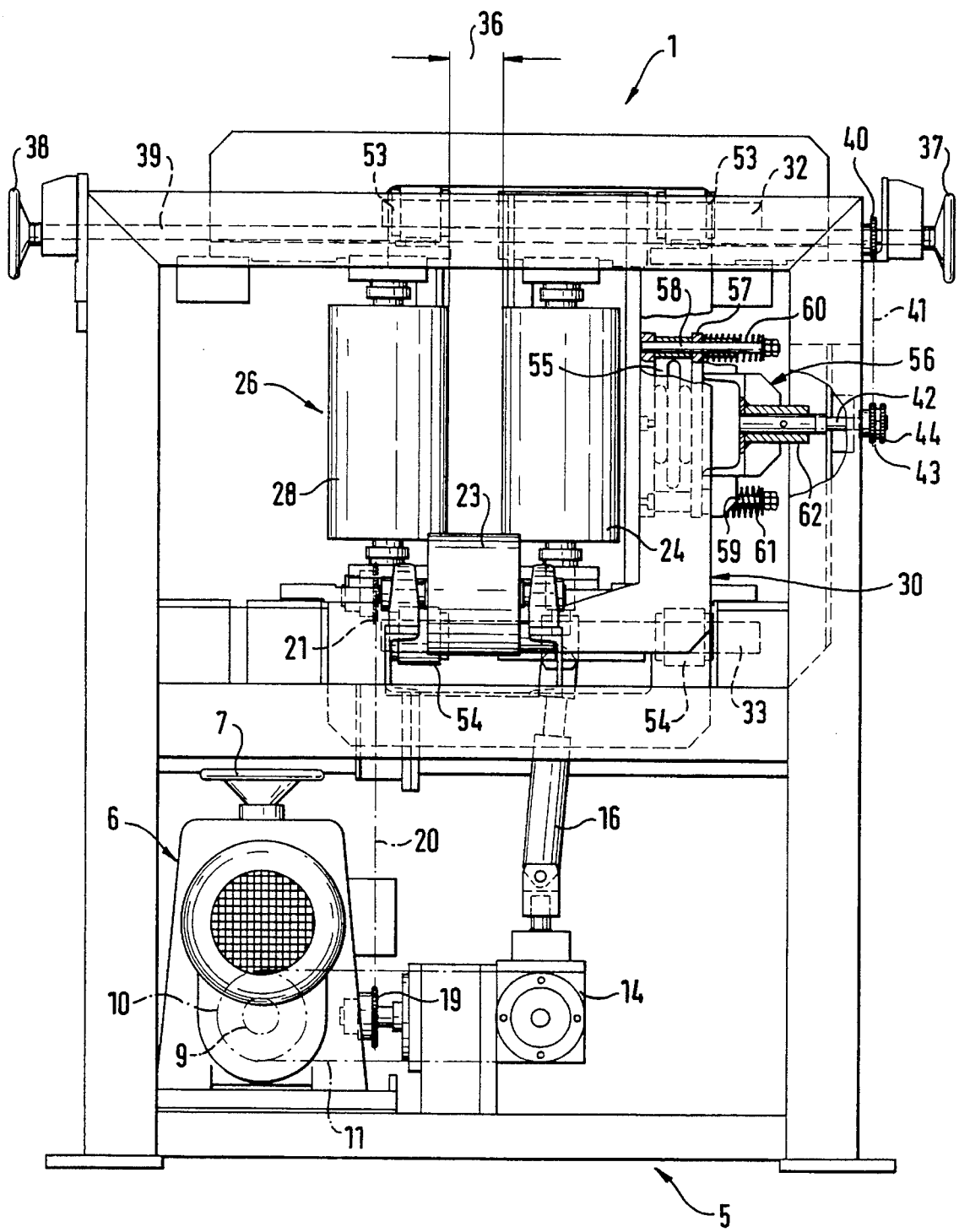
FIG. 3 is the side view of the apparatus of FIG. 1 from the left-hand side.

In the case of the example of the slide carrier 30 shown in FIG. 3 it can be seen how the slide carrier 30 is displaceably guided on each of the guide rods 32, 33 by two spaced, low-friction ball bushes 53 and 54. At its right-hand side as shown in FIG. 3 the slide carrier 30 is supported by a clamping drive 55 which is formed as a pneumatic bellows cylinder. The clamping drive 55 is for its part supported at the right-hand side of FIG. 3 by a holder 56 which comprises a head plate 57 with bores for guide bolts 58 and 59 of the slide carrier 30. Between the head plate 57 and the free end of the guide bolts 58, 59 are arranged respective compression springs 60 and 61 which urge the slide carrier 30 to the right as shown in FIG. 3 into an initial position in which, with the clamping drive 55 not actuated, the clamping rollers 24, 28 are arranged at their spacing 36 from each other.

A threaded sleeve 62 of the holder 56 has an internal thread into which an external thread on the spindle 42 is screwed. The spindle 42 is anchored in the axial direction. Rotation of the spindle 42 by the chain drive 41, 43 therefore causes all axial displacement of the unit which consists of holder 56, clamping drive 55 and slide carrier 30 with second clamping roller 24. By rotation of the spindle 42 the initial gap 36 which characterises the unclamped initial state can in this way be preset to be somewhat greater than the thickness d (FIG. 4) of the timber 2.

Figure 11:
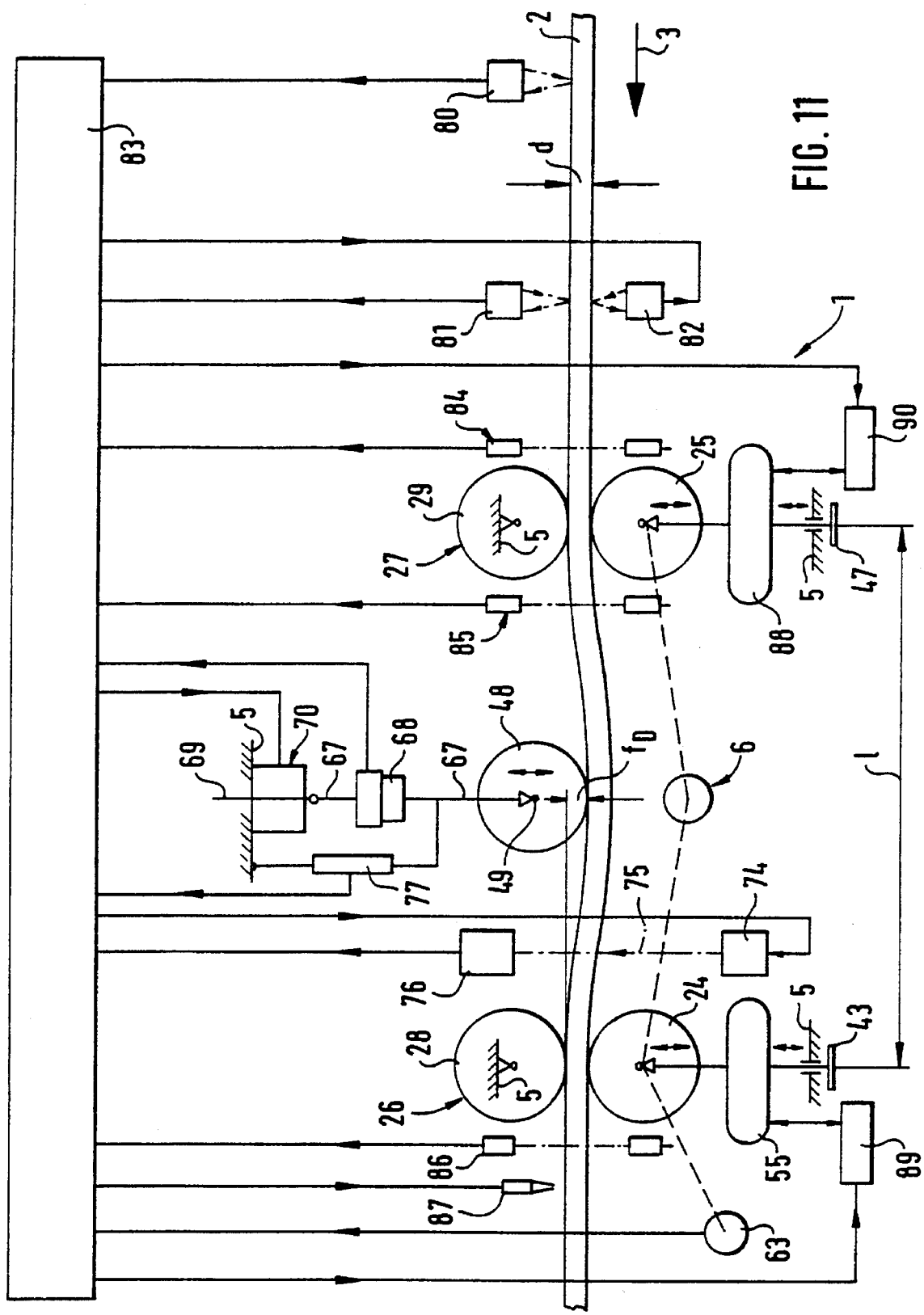
FIG. 11 is a block diagram of the apparatus shown in FIG. 1.

If then in the test procedure, when a piece of timber 2 is located between the clamping rollers 24, 28, the clamping drive 55 is actuated by introduction of compressed air, the holder 56 remains in its preset position, while the slide carrier 30 is displaced to the left as shown in FIG. 3 until the clamping rollers 24, 28 are brought into clamping contact with the timber 2. The clamping force is chosen to be large enough that in the test procedure at least approximately no slip occurs between the rotationally driven clamping roller 24 and the timber 2. This is of significance also because, as shown in FIG. 11, a rotary transducer 63 is coupled to the shaft of the clamping roller 24 and is arranged to produce electrical signals corresponding to the distance travelled by the timber 2.

As soon as the particular piece of timber 2 has left the clamping rollers 24, 28 the clamping drive 55 is depressurized, so that the compression springs 60, 61 can move the slide carrier to the right as shown in FIG. 3 back into its starting position. The second clamping roller 24 participates in this movement, so that the exit gap 36 is reproduced. During all this translatory movement of the second clamping roller 24 its rotary drive is maintained due to the universal-joint shaft 16.

Figure 4:
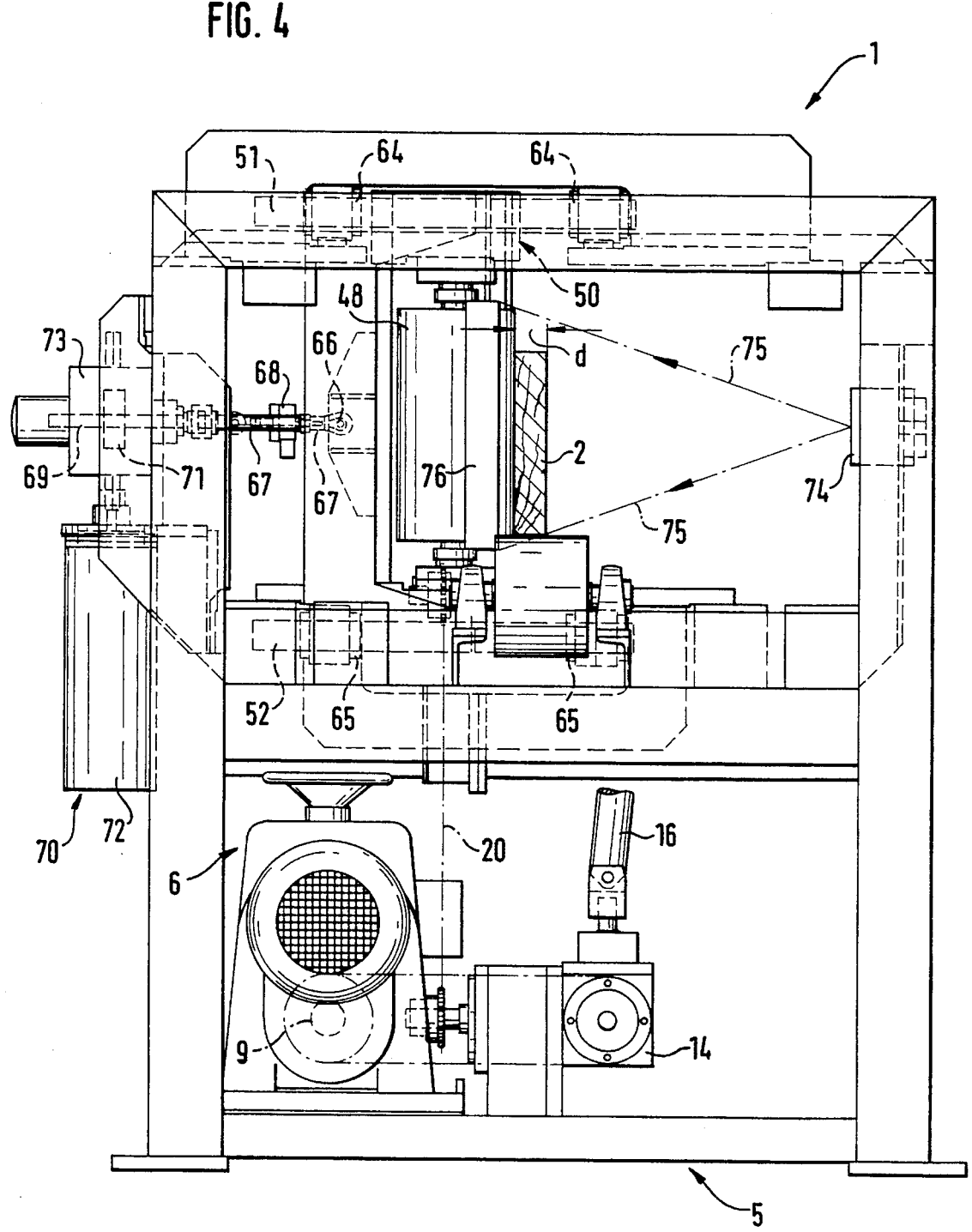
FIG. 4 is essentially the sectional view taken along the line IV—IV in FIG. 1.

As shown in FIG. 4, the slide carrier 50 is displaceable with little friction on the guide rods 51, 52 by them each having two ball bushes 64 and 65. A connecting rod 67 is coupled to the slide carrier 50 at a connecting point 66 as shown at the left-hand side of FIG. 4. In the connecting rod is set a force measuring device 68 which is here a force measuring cell. The force measuring device 68 produces electrical signals in dependence upon the restoring force which the timber deflected by the test roller 48 exerts on the test roller 48. Thanks to the solid and low friction guidance of the slide carrier 50, this restoring force is transmitted substantially completely and without adulteration to the force measuring device 68.

At the left-hand end of the connecting rod 67 as it is shown in FIG. 4 it is connected to a threaded spindle 69 of a setting drive 70 which is fixed in relation to the apparatus. The threaded spindle 69 is mounted for axial displacement but is prevented from auto-rotation. A nut 71 which is fixed in the axial direction engages with the threaded spindle 69 and is rotatably drivable from an ac servo-motor 72 by way of an angular gear 73. A rotation of the nut 71 in the one or other direction causes a corresponding translatory movement of the threaded spindle 69 and an equivalent movement of the slide carrier 50.

Figure 2:
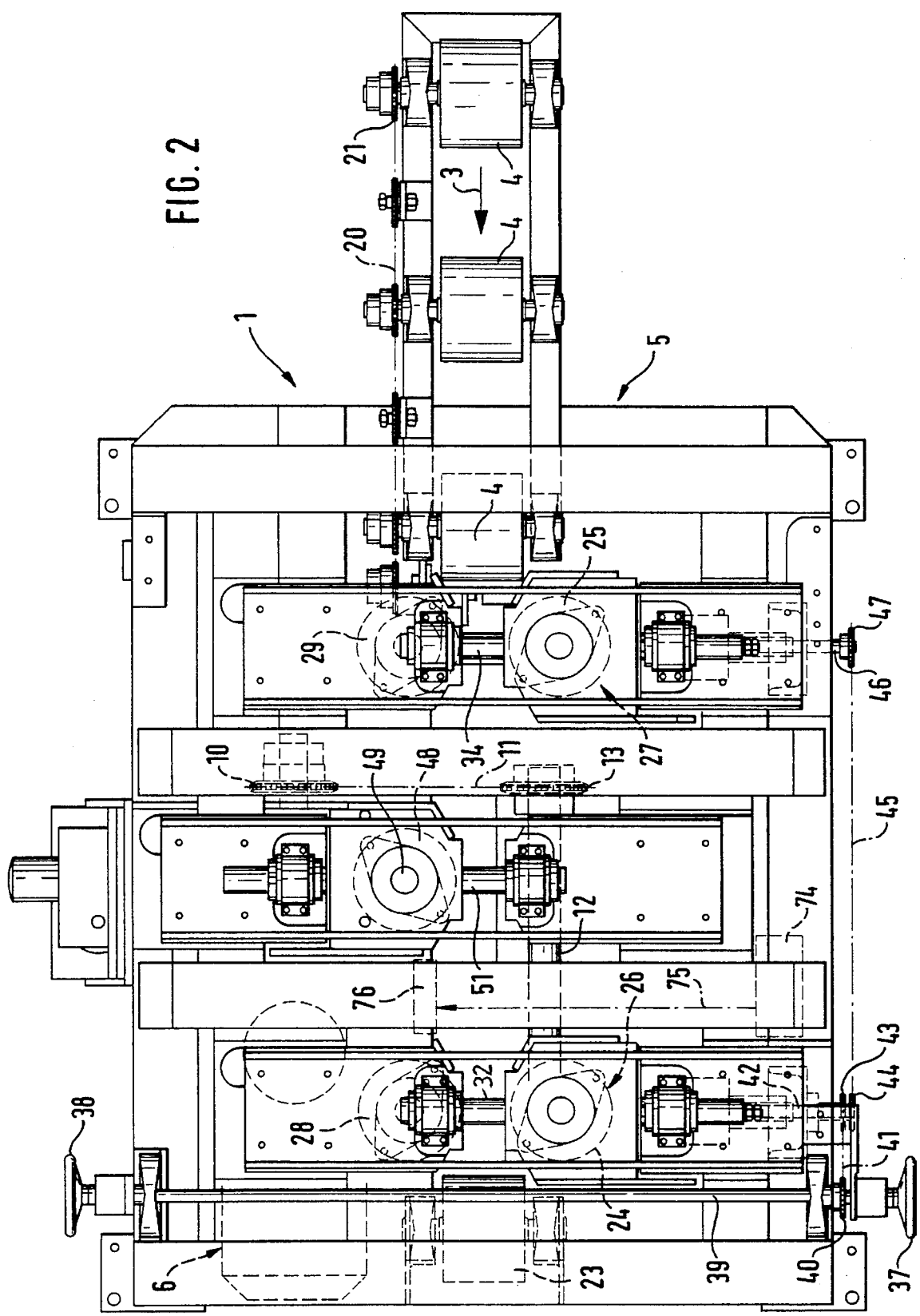
FIG. 2 is the plan view of the apparatus according to FIG. 1.

FIG. 4 also shows a radiation source 74 which is also indicated in FIG. 2 and which is here an X-ray source which emits a fan-shaped radiation beam 75 in a plane which is perpendicular to the direction of movement 3 of the timber. On the other side of the timber 2 is arranged a receiving device 76 formed as a line of receivers. The receiving device 76 produces electrical signals which correspond to the received radiation from the radiation source 74, after this has penetrated through the timber 2 and after it has been absorbed by the timber to a greater or lesser extent. In this way the overall width of the timber 2 can be sensed by the radiation beam 75 either continuously or periodically. The electrical signals produced therefrom can in a manner known per se be evaluated and conclusions can be drawn as to the presence of local knots and/or the gross density of the timber 2.

Figure 5:
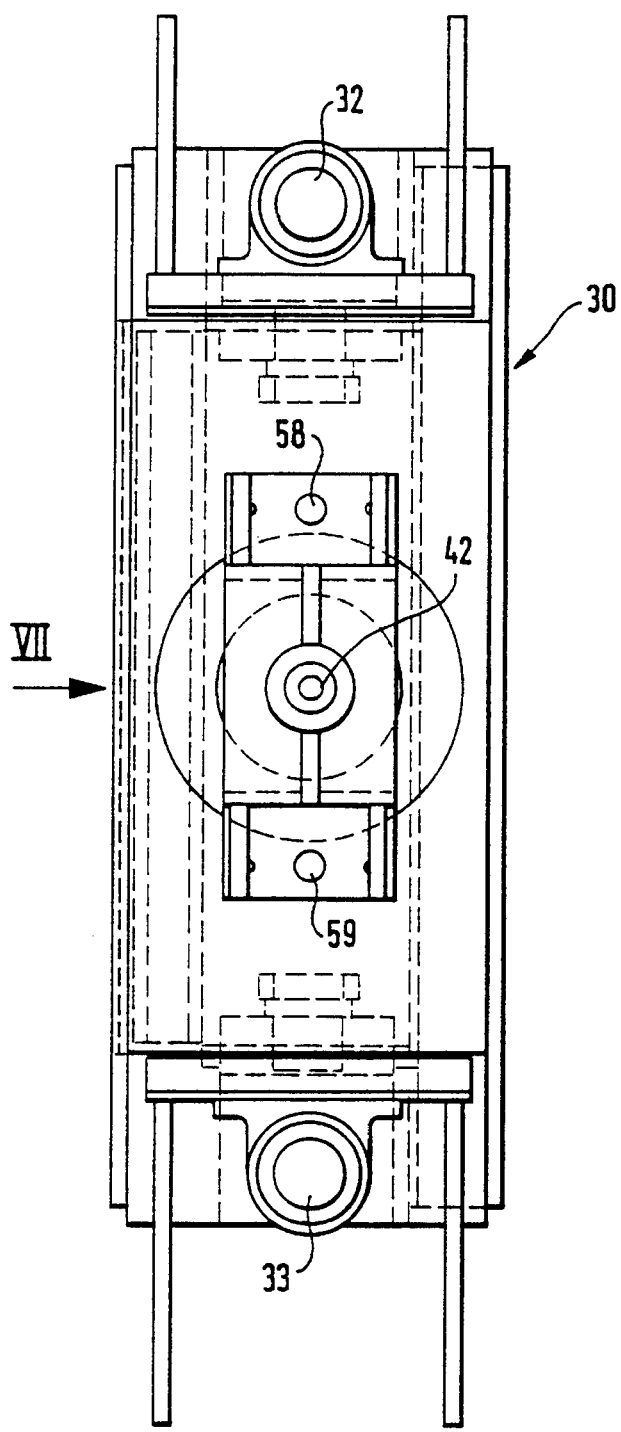
FIG. 5 is a detail plan view taken from FIG. 1, on an enlarged scale.
Figure 6:
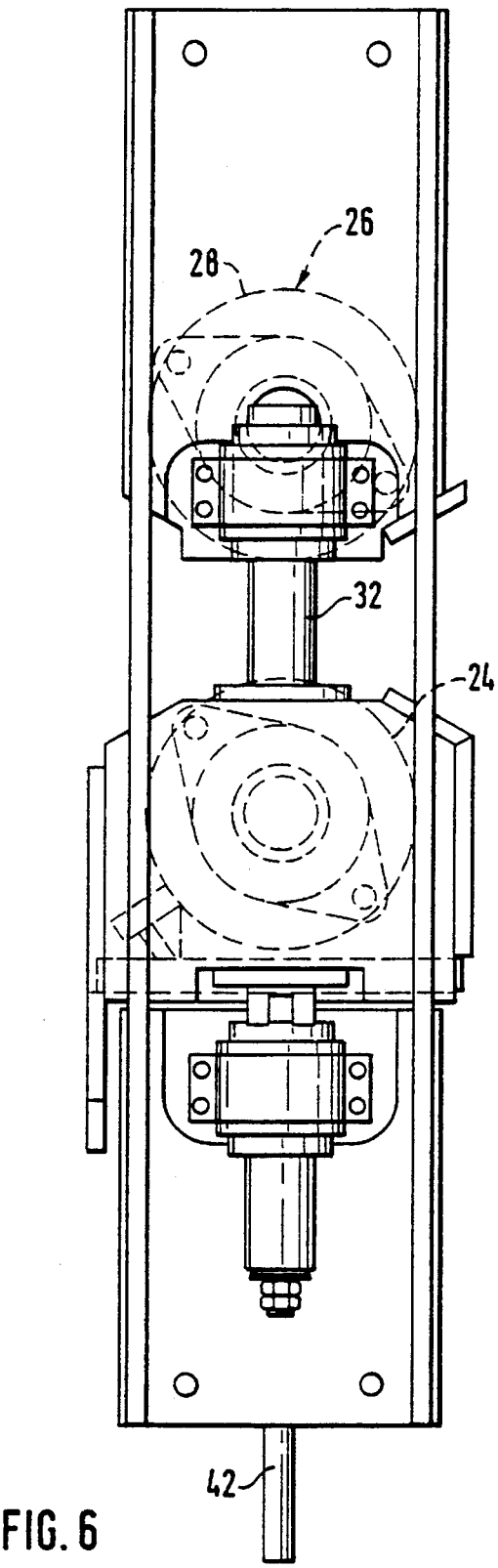
FIG. 6 is the plan view of the detail shown in FIG. 5.
Figure 7:
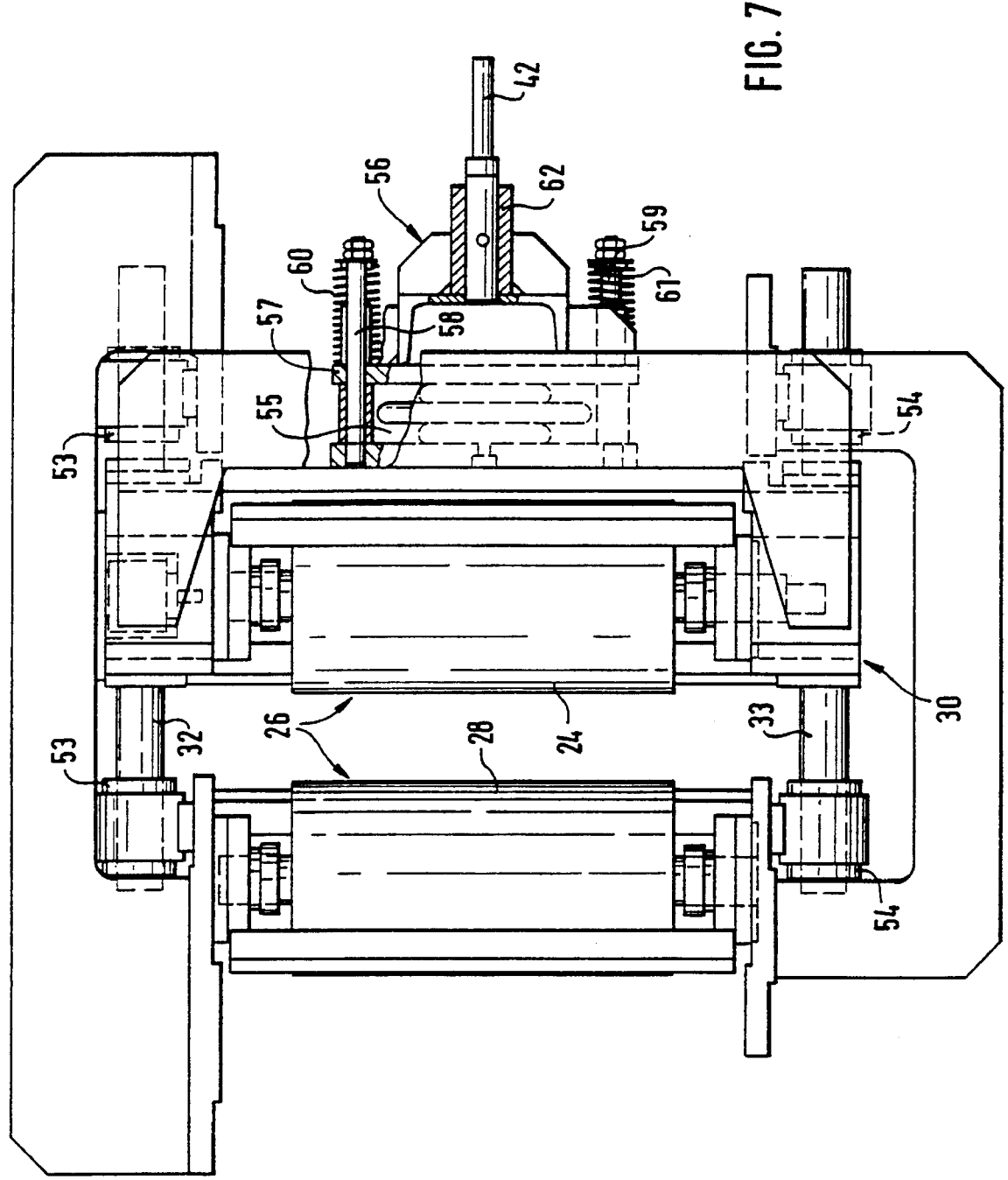
FIG. 7 is the view VII in FIG. 5.

In FIGS. 5 to 7 are shown details of the clamping roller pair 26 and of its structural environs. The structural environs of the other clamping roller pair 27 are formed in the same way and therefore do not need to be shown in detail.

Figure 8:
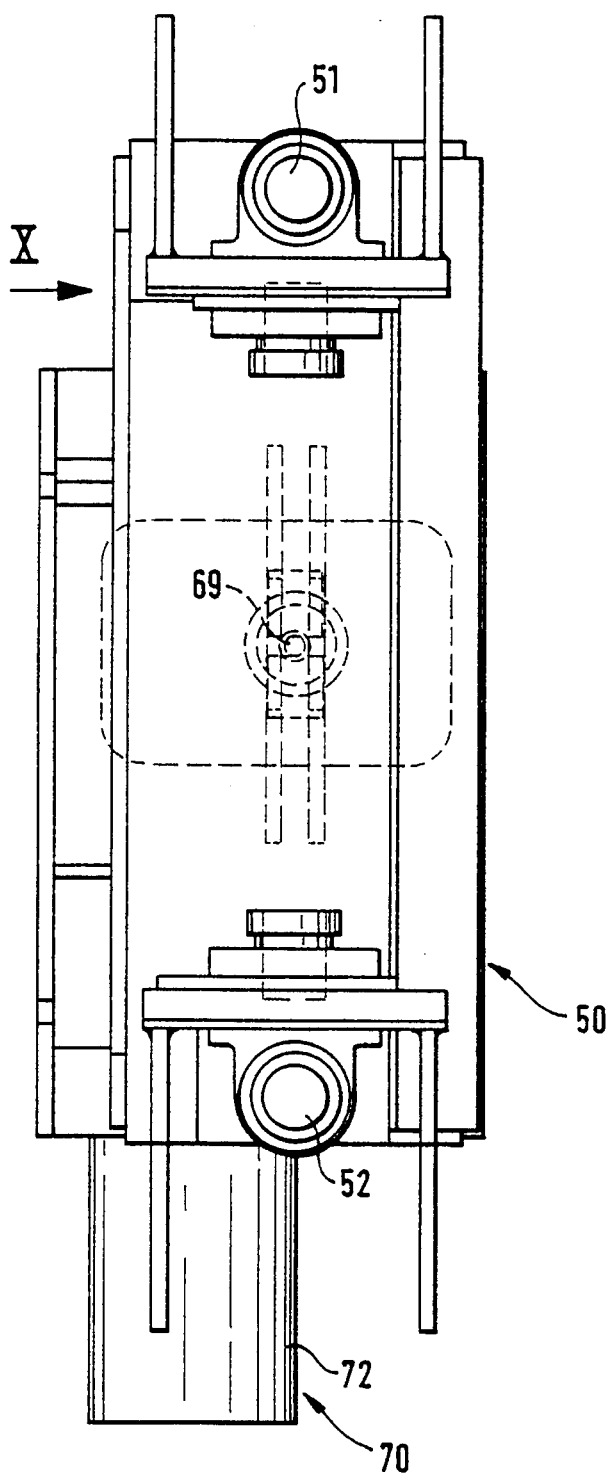
FIG. 8 is a further detail view from FIG. 1, on an enlarged scale.
Figure 9:
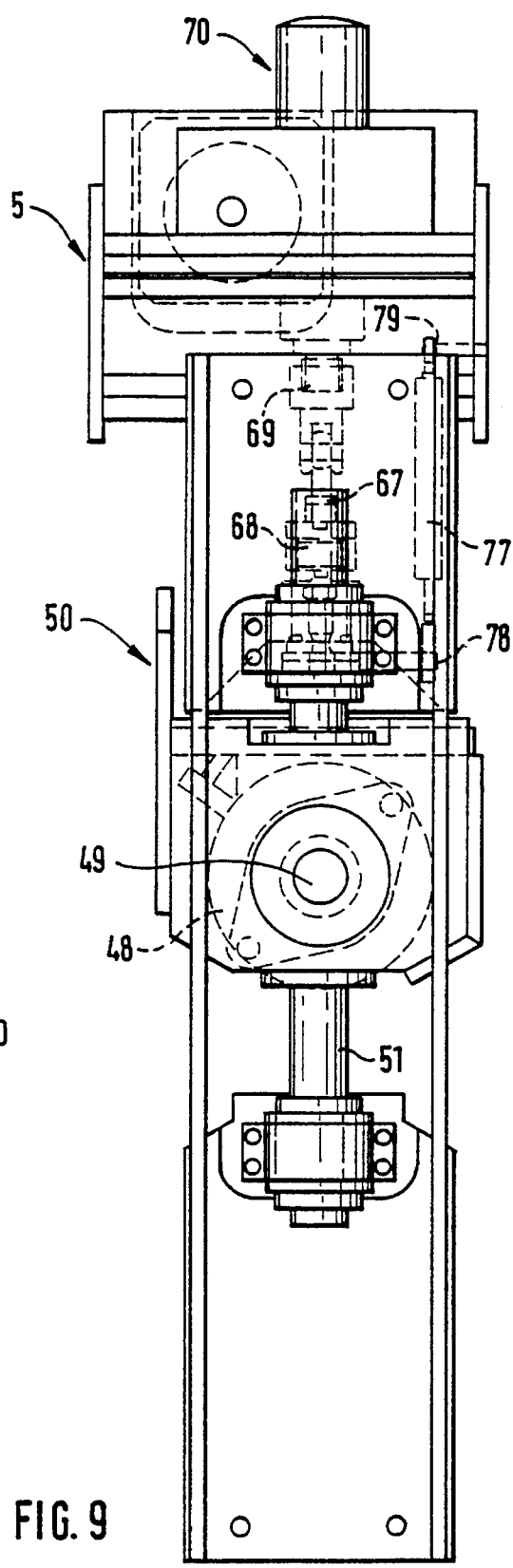
FIG. 9 is the plan view of the detail shown in FIG. 8.
Figure 10:
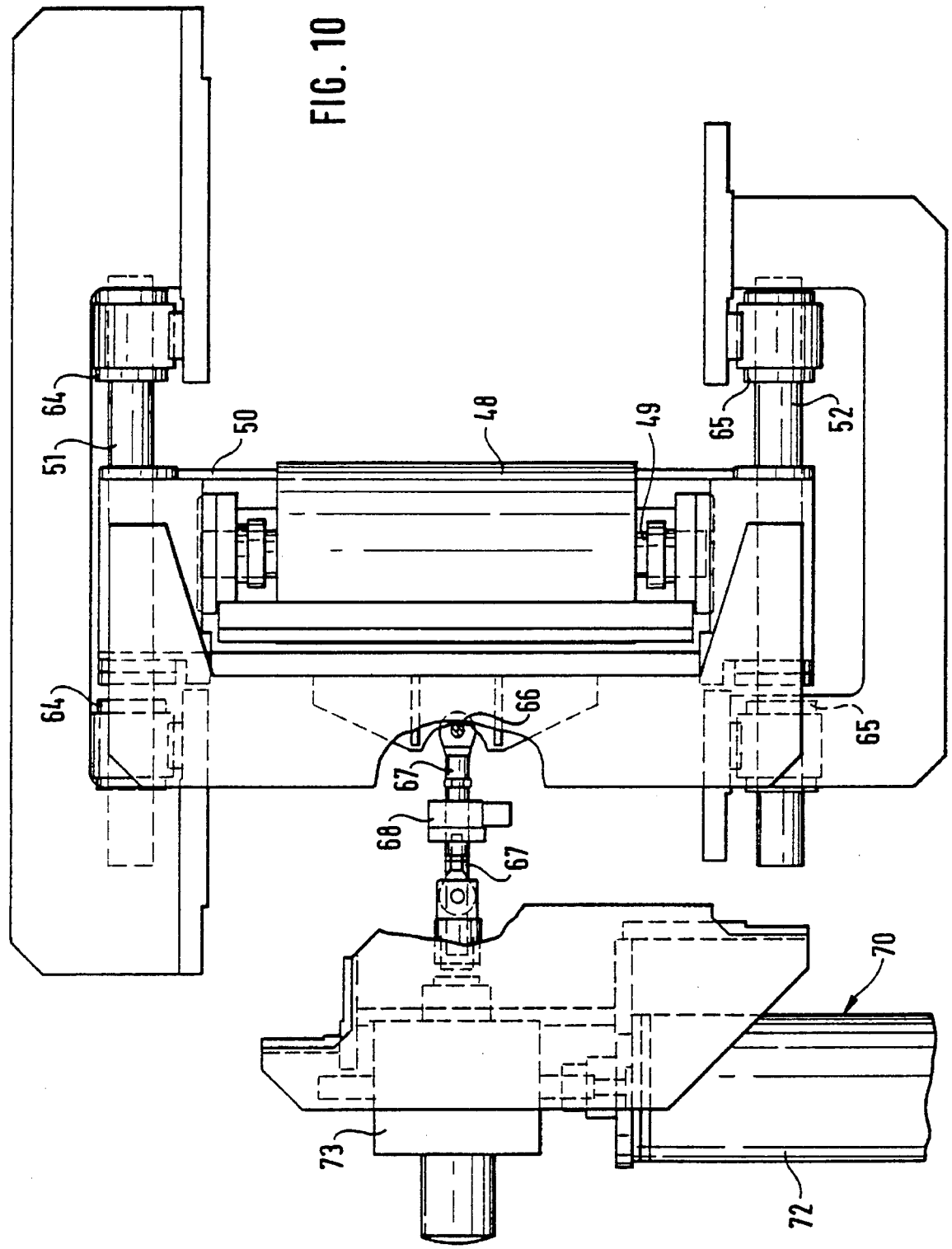
FIG. 10 is the view X in FIG. 8.

In FIGS. 8 to 10 additional details of the test roller 48 and of the adjacent structural components are illustrated.

FIG. 9 shows additionally a distance transducer 77 which is coupled on the one hand to a connection point 78 on the slide carrier 50 and on the other hand to a connection point 79 on the frame 5. The distance transducer measures the position of the test roller 48 perpendicular to the direction of movement 3 of the timber 2 and produces corresponding electrical signals.

The diagram of FIG. 11 shows in a schematic way the construction and function of the apparatus 1.

When a piece of timber 2 approaches the clamping roller pair 27 in its path of movement 3, it initially traverses a test area along which are arranged spaced measuring elements 80 and 81 for the contactless measurement of the natural curvature of the timber 2. In this way, natural curvature can be established very accurately, which includes for the timber 2 in FIG. 1 either upwards or downwards from the neutral centre position which is indicated there. Laser sensors can be uses in particular as measuring elements.

Measuring element 81 lies on the opposite side of the timber 2 to measuring element 82. The measuring heads 81, 82 serve to measure the thickness d of the timber 2. All measuring elements 80 to 82 are connected to a computer 83 and supply electrical measurement signals to the computer 83. The beginning and the end of the timber 2 actuate successive light barriers 84, 85 and 86 of the apparatus 1. These light barriers are also connected to the signal transmission system with the computer 83.

In an equivalent manner, the radiation source 74 for the control and the receiving device 76 for the signal transmission are connected to the computer 83.

By means of the computer 83 one can control a device 87 for the marking of the timber 2. The rotationally drivable incremental transducer 63, driven by the second clamping roller 24, likewise feeds its signals to the computer 83. The same goes for the force measuring device 68 and the distance transducer 77.

The clamping drive 55 for the second clamping roller 24 and a clamping drive 88 of the same type for the second clamping roller 25 are actuated by pneumatic valves 89 and 90 respectively. The valves 89, 90 are controlled by the computer 83.

The apparatus 1 functions for example as follows:

The light barrier 84 is interrupted by the leading edge of the piece of timber 2, while the second clamping rollers 24, 25 still located in the open position are driven into rotation. This has the result that the rotary transducer 63 inputs incremental signals into the computer 83. After a defined number of these increments, for a known feed speed of the timber 2, the leading end of the timber is already located just a short distance behind the clamping roller pair 27. The computer then controls the valve 90, and the clamping drive 88 is subjected to compressed air. This has the result that the second clamping roller 25 is moved into clamping contact with the timber 2 and from there participates in the feed advance of the timber 2 in its direction of movement 3. The leading end of the timber then interrupts the light barrier 85. This causes the measurement of the natural curvature of the timber 2 by the measuring elements 80, 81 and the measurement of the thickness d of the timber 2.

The leading end of the timber 2 then contacts the test roller 48 and is deflected downwards by this roller as shown in FIG. 11. The leading end of the timber 2 then passes through the fan-shaped radiation beam 75 so that from the receiving device 76 signals can be sent to the computer 83 concerning the knottiness and rough thickness of the timber 2. The leading end of the timber 2 then enters into the clamping roller pair 26, whose second clamping roller 24 is still located in the opening position. Shortly thereafter, after a corresponding number of increments, the valve 89 is activated by the computer 83 and subjects the clamping drive 55 to compressed air. This has the result that the second clamping roller 24 is driven into clamping contact with the timber 2. Shortly after this, the leading end of the timber 2 interrupts the light barrier 86, with the result that the force measurement by the force measuring device 68 and the displacement measurement of the distance transducer 77 are begun. Because of the pre-setting of the test roller 48 by the threaded spindle 69, an imposed bending deflection $f_D$ is imparted to the timber 2 in the plane of the test roller 48. The aim is to maintain this imposed deflection $f_D$ at least approximately constant. This is established by control of the setting drive 70 by the computer 83 having regard to the natural curvature of the timber 2 as established by the measuring elements 80 and 81. Thus, the actual position of the test roller 48 transversely to the direction of movement 3 of the timber 2 is continuously transmitted by the displacement transducer 77 to the computer 83.

The magnitude of the imposed deflection $f_D$ is chosen in dependence above all on the thickness d of the timber 2 so that the effect on the timber 2 is not too trifling but also so that the timber is not over-stressed.

The modulus of elasticity in flexure is calculated by the computer 83 at particular distances, for example every 10 mm along the length of the timber, from the restoring force resulting from the imposed bending deflection $f_D$. This information is combined by the computer 83 with the strength information obtained from the irradiation by the fan-shaped radiation beam 75 over the full length of the timber. From this combination is obtained a combined strength value which is compared with the limits of sorting classes which have previously been programmed in. The result can be marked in a suitable manner on the timber 2 by the marking device 87 in order to facilitate the subsequent sorting after classification sorting, possibly according to preset quality control limits.

A mathematical relationship for the modulus of elasticity in flexure (E) for the typically shaped timber is:

$$E = \frac{F \cdot l^3}{48 \cdot (f_D \pm f_N) \cdot \frac{h \cdot d^3}{12}} \quad [\text{N/mm}^2]$$

wherein
F= the particular restoring force
l= the span between the clamping roller pairs (26, 27)
$f_D$=the bending deflection of the timber (2) imposed by the pressure of the test roller (48)
$f_N$=the natural curvature of the timber (2)
h= the width of the timber (2) entered into the computer (83) and
d= the particular thickness of the timber.

A passage of the end of the timber 2 through the apparatus 1 has the result of successively terminating the functions which have previously been activated.

Figure 12:
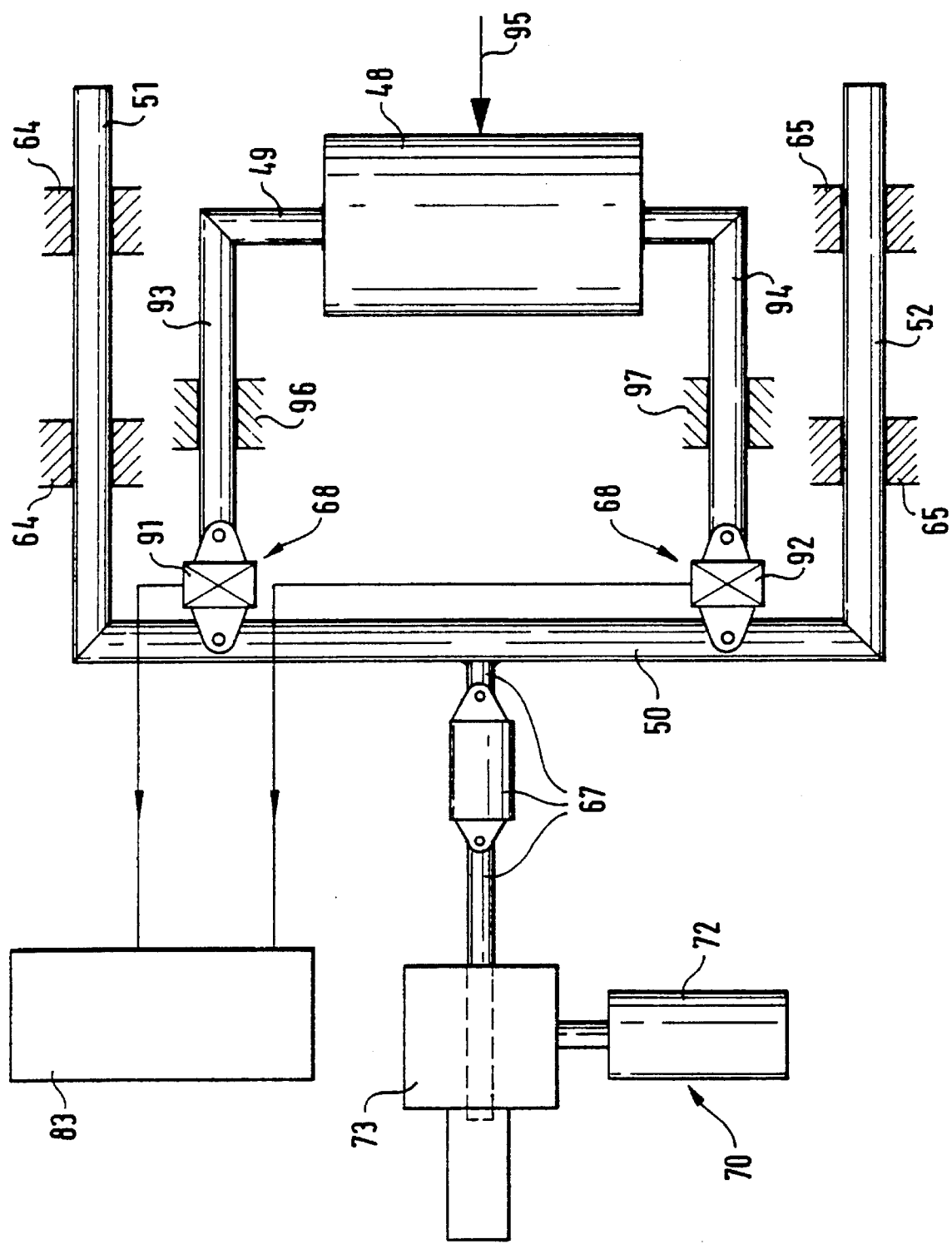
FIG. 12 is a schematic illustration of another embodiment of the test roller mounting.

FIG. 12 shows another embodiment of the support for the shaft 49 of the test roller 48. The force measuring device is not integrated into the connecting rod 67 in FIG. 12 as it is in FIG. 10. Instead, the force measuring device 68 according to FIG. 12 comprises two force measuring elements 91 and 92 which are each coupled on the one hand to the slide 50 and on the other to a guide rod 93 and 94. Each guide rod 93, 94 is fixed to one end of the shaft 49.

The resulting force is indicated by an arrow 95 and is exerted on the test roller 48 by the timber which is not shown in FIG. 12. The resulting force 95 acts, as shown in FIG. 12, at the longitudinal centre of the test roller 48. Even if this should no longer be the case, due to changing dimensions of the timber, and the resulting force acts on one side or the other of the longitudinal centre of the roller 48, a trouble-free force measurement would still be guaranteed, since tilting on the one hand would be excluded on the one hand by the ball bushes 64, 65 on the guide rods 51, 52 and on the other hand by the ball bushes 96 and 97 on the guide rods 93, 94.

In the embodiment according to FIG. 12 those components which are the same as in the embodiment previously described above are indicated by the corresponding same reference numerals.

We claim:

1. A process for machine sorting sawn timber according to strength, comprising the steps of:

(a) moving the timber relative a test roller;
    (b) supporting the timber with two pairs of clamping rollers, said test roller positioned between said pairs of clamping rollers;
    (c) pressing said test roller into continuous contact with the timber to impose an approximately constant bending deflection thereto, said test roller being pressed against the timber by a setting drive;
    (d) periodically measuring a restoring force exerted by the timber on said test roller as a result of said bending deflection, said periodic measuring being taken along the length of the timber in its direction of motion, and feeding signals corresponding to the restoring force measurement to a computer for use in calculating the local strength;
    (e) measuring a natural curvature of the timber and feeding signals corresponding to said curvature measurement to the computer; and
    (f) measuring the position of said test roller transversely to the direction of movement of the timber and feeding signals corresponding to said position measurement to the computer.

2. A process according to claim 1 wherein the magnitude of the imposed bending deflection is chosen depending upon the timber under test so that the timber is not stressed too little but also is not overstressed.

3. A process according to claim 1 wherein a working point for the setting of the test roller transversely to the direction of movement of the timber is maintained at least approximately in the optimum region of the stress/extension curve of the timber.

4. A process according to claim 1 wherein each said clamping roller pair comprises clamping rollers which are adjusted to an initial gap from one another which is at least equal to the particular timber thickness, and wherein each said clamping roller pair is first actuated for the clamping of the timber when the leading edge of the timber has passed the relevant clamping roller pair.

5. A process according to claim 4 wherein the initial gap of said clamping rollers of each said clamping roller pair is reproduced as soon as the trailing edge of the timber has left the clamping roller pair.

6. A process according to claim 1 wherein the natural curvature of the timber is measured without contact.

7. A process according to claim 1 further comprising the step of measuring a thickness of said timber and feeding signals corresponding to said thickness to said computer.

8. A process according to claim 1 wherein the computer periodically calculates the local modulus of elasticity in flexure (E) of the timber according to the following equation:

$$E = \frac{F \cdot l^3}{48 \cdot (f_D \pm f_N) \cdot \frac{h \cdot d^3}{12}} \quad [\text{N/mm}^2]$$

wherein
F= the particular restoring force
l= the span between the clamping roller pairs (26, 27)
$f_D$=the bending deflection of the timber (2) imposed by the pressure of the test roller (48)
$f_N$= the natural curvature of the timber (2)
h= the width of the timber (2) entered into the computer (83) and
d= the particular thickness of the timber.

9. A process according to claim 1 further comprising the steps of locally irradiating the timber and detecting the radiation having passed through the timber, and feeding electrical signals corresponding to the detected radiation to said computer for determining the local knottiness and/or the local gross density.

10. A process according to claim 9 wherein the timber is irradiated by X-rays and wherein the X-rays having passed through the timber are detected by a line of receivers arranged transversely to the direction of movement of the timber.

11. A process according to claim 9 wherein the local modulus of elasticity in flexure (E) as well as the local knottiness and/or the local gross density of the timber are combined together by computation and are used jointly for the establishment of the local strength of the timber.

12. A process according to claim 11 wherein a minimum local strength of a piece of timber is determined by the computer and is compared with sorting classes established by bands of strength values, and thereafter the timber is sorted into the relevant sorting classes.

13. A process according to claim 11 wherein on the occurrence of variations in the local strength of a piece of timber, appropriate qualitative or sorting classes and their limits are identified for the timber and subsequently are used for the cutting-up of this timber and the dividing of the timber into timber parts of different sorting classes.

14. A process according to claim 2 wherein the working point for the setting of the test roller transversely to the direction of movement of the timber is maintained at least approximately in the optimum region of the stress/extension curve of the timber.

15. A process according to claim 10 wherein the local modulus of elasticity in flexure (E) as well as the local knottiness and/or the local gross density of the timber are combined together by computation and are used jointly for the establishment of the local strength of the timber.

16. An apparatus for machine sorting of sawn timber according to strength, comprising:

two pairs of clamping rollers arranged spaced from one another for supporting and advancing the timber in a direction of movement;

a rotatably mounted test roller arranged between said pairs of clamping rollers, said test roller having a shaft which is moveable transversely to the direction of movement of the timber so as to move said shaft against the timber to impose a bending deflection on the timber;

a setting drive arranged to press said test roller into continuous contact with the timber during the measurement process, said setting drive being controllable;

means for controlling said setting drive so that the bending deflection imposed by the test roller remains approximately constant during the measuring process;

a force measuring device positioned to measure a restoring force exerted by the timber on said test roller resulting from said bending deflection, said measuring device including means for feeding signals corresponding to the restoring force measured to a computer;

means for measuring the natural curvature of the timber and feeding signals corresponding to the curvature measurement to the computer; and means for measuring the position of the test transversely to the direction of movement of the timber and for feeding corresponding position signals to the computer.

17. An apparatus according to claim 16 wherein each said clamping roller pair comprises a first clamping roller rotatably mounted in a fixed position on the apparatus, a second clamping roller rotatably mounted on slide means associated therewith and displaceable transversely to the direction of movement of the timber, wherein at least one said clamping roller is rotatably drivable; and wherein each said slide means is displaceable by a controllable clamping drive.

18. An apparatus according to claim 17 wherein each said clamping drive is supported by a holder associated therewith, and each holder is pre-settable in the direction of displacement of the associated slide means depending upon the particular timber thickness.

19. An apparatus according to claim 18 wherein between each slide means and the associated holder there is provided spring means by which the slide means is urged in a direction of opening away from the first clamping roller.

20. An apparatus according to claim 16 wherein said means for measuring the natural curvature of the timber comprises at least two measuring elements arranged spaced from one another in the direction of movement of the timber and positioned in advance of said clamping roller pairs relative to the direction of movement of the timber, and wherein said measuring elements comprise means for measuring the curvature without contacting the timber, and each measuring element produces electrical measured signals and is connected to the computer.

21. An apparatus according to claim 16 further comprising two timber thickness measuring elements having means for measuring the thickness without contacting the timber, said two elements being arranged apart from each other at a greater distance than the timber thickness transversely to the direction of movement of the timber, and each measuring element produces electrical measurement signals and is connected to the computer.

22. An apparatus according to claim 16 further comprising:

a radiation source arranged to irradiate the timber transversely to its direction of movement, receiving means for radiation which has passed through the timber arranged on a side of the timber which is remote from the radiation source, and wherein the receiving means produces electrical signals corresponding to the detected radiation, and useable for determining local knottiness and/or local density of the timber and is connected to the computer.

23. An apparatus according to claim 22 wherein the radiation source is an X-ray source which emits a fan of radiation in a plane which is at least approximately perpendicular to the direction of movement of the timber, and the receiving means comprises a line of receivers arranged in this plane.

24. An apparatus according to claim 23 wherein said receiving means comprises a line of receivers which senses the full width of the timber.

25. An apparatus according to claim 16 wherein the test roller is rotatably mounted on a slide carriage which is displaceable transversely to the direction of movement of the timber, and a connecting rod incorporating the force measuring device is coupled to the slide carriage and is displaceable by the setting drive which is fixed in position on the apparatus.

26. An apparatus according to claim 16 wherein the setting drive which is fixed in position on the apparatus is connected by means of a connecting rod to a slide carriage which is displaceable transversely to the direction of movement of the timber, and the two ends of the shaft of the test roller are respectively supported on the slide carriage by respective force measuring elements of the force measuring device.

27. An apparatus according to claim 25 wherein the setting drive comprises an ac servo-motor which is controllable by the computer in order to maintain an at least approximately constant bending of the timber imposed by the test roller.

28. An apparatus according to claim 25 wherein the means for measuring the position of the test roller comprises a displacement transducer which is mounted on the one hand on the slide carriage and on the other hand fixedly on the apparatus.

29. An apparatus according to claim 16 wherein at an exit from the apparatus there is provided means controllable by the computer for marking the passed timber.

30. An apparatus according to claim 26 wherein the setting drive comprises an ac servo-motor which is controlled by the computer in order to maintain the constant bending of the timber imposed by the test roller.

31. An apparatus according to claim 26 wherein the means for measuring the position of the test roller comprises a displacement transducer which is mounted on the one hand on the slide carriage and on the other hand fixedly on the apparatus.

* * * * *